(12) United States Patent
Nakanishi (10) Patent No.: US 11,300,528 B2
(45) Date of Patent: Apr. 12, 2022

(54) X-RAY COMPUTED TOMOGRAPHY APPARATUS

(71) Applicant: Toshiba Medical Systems Corporation, Otawara (JP)

(72) Inventor: Satoru Nakanishi, Utsunomiya (JP)

(73) Assignee: Canon Medical Systems Corporation, Otawara (JP)

(*) Notice: Subject to any disclaimer, the term of this patent is extended or adjusted under 35 U.S.C. 154(b) by 80 days.

(21) Appl. No.: 15/711,619

(22) Filed: Sep. 21, 2017

(65) Prior Publication Data

US 2018/0088061 A1 Mar. 29, 2018

(30) Foreign Application Priority Data

Sep. 26, 2016 (JP) .............................. JP2016-186936

(51) Int. Cl.
*A61B 6/03* (2006.01)
*G01N 23/046* (2018.01)
*A61B 6/00* (2006.01)
*A61B 6/02* (2006.01)

(52) U.S. Cl.
CPC .......... *G01N 23/046* (2013.01); *A61B 6/027* (2013.01); *A61B 6/032* (2013.01); *A61B 6/542* (2013.01); *A61B 6/488* (2013.01)

(58) Field of Classification Search
CPC ...... G01N 23/046; A61B 6/542; A61B 6/027; A61B 6/032
See application file for complete search history.

(56) References Cited

U.S. PATENT DOCUMENTS

| 5,379,333 A | * | 1/1995 | Toth | ........................ | A61B 6/032 |
| | | | | | 378/108 |
| 5,949,811 A | * | 9/1999 | Baba | ..................... | A61B 6/4225 |
| | | | | | 378/108 |
| 2003/0095624 A1 | * | 5/2003 | Eberhard | ............... | A61B 6/502 |
| | | | | | 378/37 |
| 2003/0185343 A1 | | 10/2003 | Horiuchi | | |

FOREIGN PATENT DOCUMENTS

| JP | 2001-190543 | 7/2001 |
| JP | 2003-290214 | 10/2003 |
| JP | 2009-131563 | 6/2009 |
| JP | 2010-214091 A | 9/2010 |

OTHER PUBLICATIONS

Japanese Office Action dated Aug. 11, 2020, issued in Japanese Patent Application No. 2016-186936.

* cited by examiner

*Primary Examiner* — David P Porta
*Assistant Examiner* — Shun Lee
(74) *Attorney, Agent, or Firm* — Oblon, McClelland, Maier & Neustadt, L.L.P.

(57) ABSTRACT

According to one embodiment, an X-ray computed tomography apparatus includes an X-ray detector, data acquisition circuitry, and processing circuitry. The X-ray detector detects X-rays emitted by an X-ray tube and transmitted through an object and outputs an electrical signal concerning the detected X-rays. The data acquisition circuitry amplifies the electrical signal by a variable gain and acquires detection data based on the amplified electrical signal. The processing circuitry decides the gain and a modulation condition of a tube current in directional modulation scan based on body thickness information of the object.

10 Claims, 6 Drawing Sheets

X-RAY COMPUTED TOMOGRAPHY APPARATUS

CROSS-REFERENCE TO RELATED APPLICATIONS

This application is based upon and claims the benefit of priority from the prior Japanese Patent Application No. 2016-186936, filed Sep. 26, 2016 the entire contents of which are incorporated herein by reference.

FIELD

Embodiments described herein relate generally to an X-ray computed tomography apparatus.

BACKGROUND

In X-ray computed tomography, directional modulation scan (XY modulation) is performed to reduce an X-ray dose. The directional modulation scan is a technique of estimating object body thicknesses in the LR direction and the AP direction from scanogram images and the like and modulating a tube current in accordance with an irradiation direction (rotation angle) during one revolution of an X-ray source.

The directional modulation scan is used in helical scan as well. Additionally, to increase a DAS output value without increasing the X-ray dose, a DAS gain is changed in some cases. A shoulder portion is flat in a slice (axial section). Hence, the tube current value is set to a large value in the LR direction. On the other hand, the shoulder portion is thin in the AP direction in a slice. Hence, if the shoulder portion is irradiated with X-rays in the LR direction, a high dose of direct rays enters an X-ray detector and readily causes overflow. To avoid the overflow, the DAS gain cannot be raised. As a result, a low count artifact derived from DAS linearity readily occurs in the abdominal portion or pelvis where the object body thickness is large.

DETAILED DESCRIPTION

An X-ray computed tomography apparatus according to the embodiment includes an X-ray detector, data acquisition circuitry, and processing circuitry. The X-ray detector detects X-rays emitted by an X-ray tube and transmitted through an object and outputs an electrical signal concerning the detected X-rays. The data acquisition circuitry amplifies the electrical signal by a variable gain and acquires detection data based on the amplified electrical signal. The processing circuitry decides the gain and a modulation condition of a tube current in directional modulation scan based on body thickness information of the object.

An X-ray computed tomography apparatus according to the embodiment will now be described with reference to the accompanying drawings.

Figure 1:
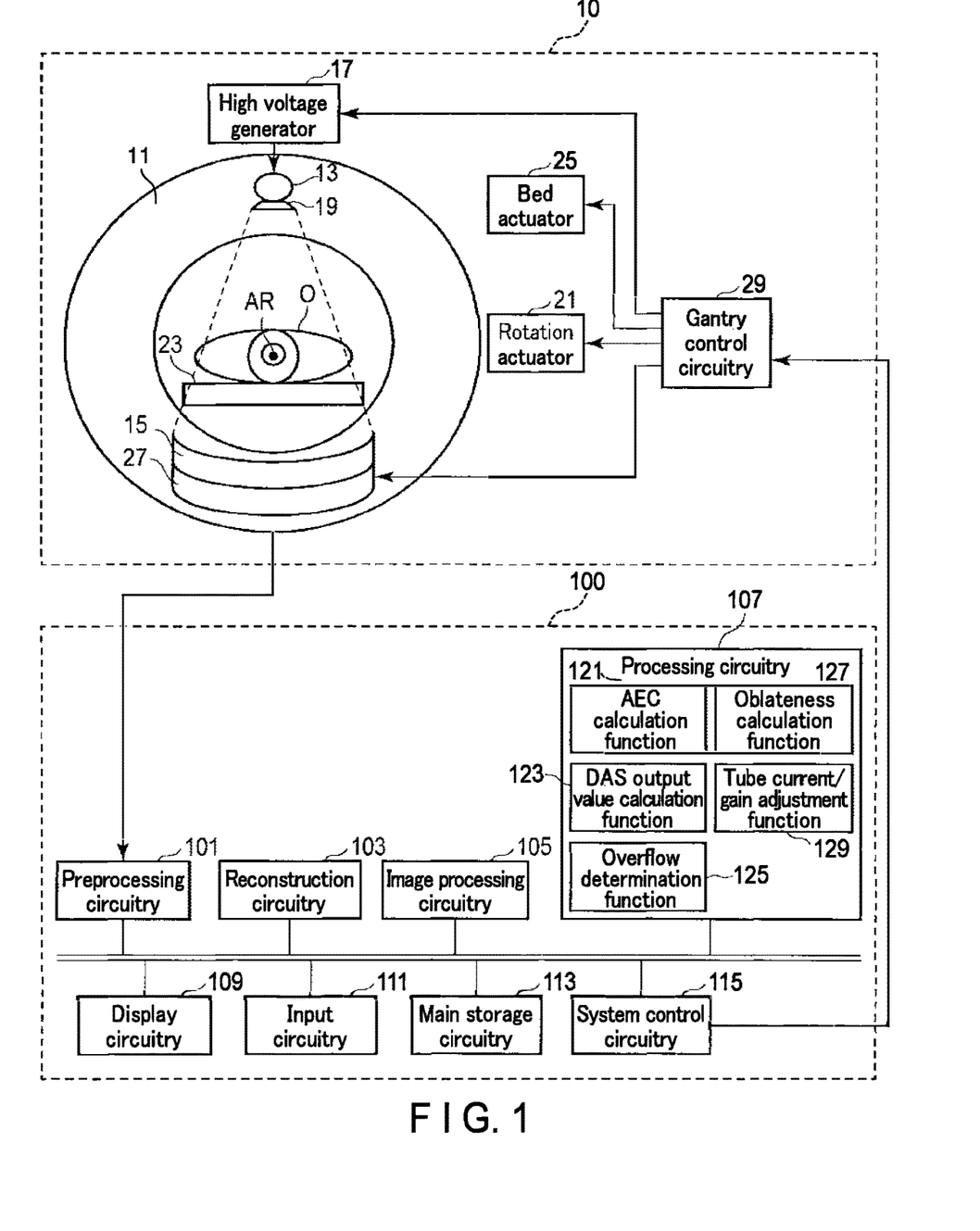
FIG. 1 is a block diagram showing the arrangement of an X-ray computed tomography apparatus according to the embodiment.

FIG. 1 is a block diagram showing the arrangement of the X-ray computed tomography apparatus according to the embodiment. As shown in FIG. 1, the X-ray computed tomography apparatus according to the embodiment includes a gantry 10 and a console 100. For example, the gantry 10 is installed in a CT examination room, and the console 100 is installed in a control room adjacent to the CT examination room. The gantry 10 and the console 100 are connected to be communicable with each other. The gantry 10 includes a scan mechanism configured to perform X-ray CT scan of an object O. The console 100 is a computer that controls the gantry 10.

As shown in FIG. 1, the gantry 10 includes an almost cylindrical rotation frame 11 with a bore that forms an FOV (Field Of View). As shown in FIG. 1, an X-ray tube 13 and an X-ray detector 15 which are arranged to face each other via the bore are attached to the rotation frame 11. The rotation frame 11 is a metal frame made of a metal such as aluminum into an annular shape. The gantry 10 includes a main frame made of a metal such as aluminum, as will be described later. The rotation frame 11 is supported by the main frame via a bearing and the like to be rotatable about a center axis AR. A slip-ring (not shown) is provided on the contact portion of the main frame to the rotation frame 11. A conductive brush (not shown) is attached to the contact portion to be in slidable contact with the slip-ring. Power from a power supply unit (not shown) stored in the gantry 10 is supplied via the slip-ring and a sliding element to various kinds of devices such as the X-ray detector 15 and a high voltage generator 17 mounted on the rotation frame 11.

The X-ray tube 13 is connected to the high voltage generator 17. The high voltage generator 17 is attached to, for example, the rotation frame 11. The high voltage generator 17 generates a high voltage to be applied to the X-ray tube 13 from the power supplied from the power supply unit (not shown) of the gantry via the slip-ring and the sliding element and supplies a filament heating current under the control of gantry control circuitry 29. The high voltage generator 17 and the X-ray tube 13 are connected via a high voltage cable (not shown). The high voltage generated by the high voltage generator 17 is applied between an anode and a cathode stored in the X-ray tube 13 via the high voltage cable. The filament heating current generated by the high voltage generator 17 is applied to the cathode of the X-ray tube 13 via the high voltage cable. The high voltage applied between the anode and the cathode of the X-ray tube 13 is called a tube voltage. A flow of thermoelectrons that are generated from the cathode heated by the filament heating current and fly to the anode under the high voltage is called a tube current. The high voltage generator 17 adjusts the tube voltage and the tube current to the X-ray tube 13 in accordance with an X-ray condition.

A bow-tie filter 19 is attached to the X-ray emission window of the X-ray tube 13. The bow-tie filter 19 is an X-ray filter containing an X-ray attenuation substance and formed into a bow-tie shape so as to decrease the dose as the fan angle increases from the center line of X-rays.

The rotation frame 11 rotates about the center axis AR at a predetermined angular velocity upon receiving power from a rotation actuator 21. As the rotation actuator 21, an arbitrary motor such as a direct drive motor or a servo motor is used. The rotation actuator 21 is stored in, for example, the gantry 10. Upon receiving a driving signal from the gantry control circuitry 29, the rotation actuator 21 generates power to rotate the rotation frame 11.

An FOV is set in the bore of the rotation frame 11. A bed top supported by a bed 23 is inserted into the bore of the rotation frame 11. The object O is placed on the bed top. The bed 23 movably supports the bed top. A bed actuator 25 is stored in the bed 23. Upon receiving a driving signal from the gantry control circuitry 29, the bed actuator 25 generates power to move the bed 23 in the longitudinal direction, the vertical direction, and the widthwise direction. The bed top is positioned such that the imaging portion of the object O placed on it is included in the FOV.

The X-ray detector 15 detects the X-rays generated by the X-ray tube 13. More specifically, the X-ray detector 15 includes a plurality of detector elements arranged on a two-dimensional curved surface. Each detector element includes a scintillator and a photoelectric conversion element. The scintillator is made of a substance that converts X-rays into fluorescence. The scintillator converts incident X-rays into a number of fluorescent photons corresponding to the intensity of the incident X-rays. The photoelectric conversion element is a circuitry element that amplifies fluorescence and converts it into an electrical signal. As the photoelectric conversion element, for example, a photomultiplier, a photodiode, or the like is used. Note that the detector element can be either of an indirect detection type that converts X-rays into light and then detects the light, as described above, or of a direct conversion type that directly converts X-rays into an electrical signal. As the detector element of the direct detection type, for example, a type including a semiconductor diode formed by attaching electrodes to two terminals of a semiconductor is applicable.

Data acquisition circuitry 27 is connected to the X-ray detector 15. The data acquisition circuitry 27 reads, from the X-ray detector 15, an electrical signal corresponding to the intensity of X-rays detected by the X-ray detector 15, amplifies the read electrical signal by a variable gain, and acquires raw data having a digital value corresponding to the dose of X-rays during a view period. The data acquisition circuitry 27 includes, for example, DAS elements as many as the detector elements of the X-ray detector 15. For example, the plurality of detector elements and the plurality of DAS elements are connected in a one-to-one correspondence. The raw data is also called detection data.

Figure 2:
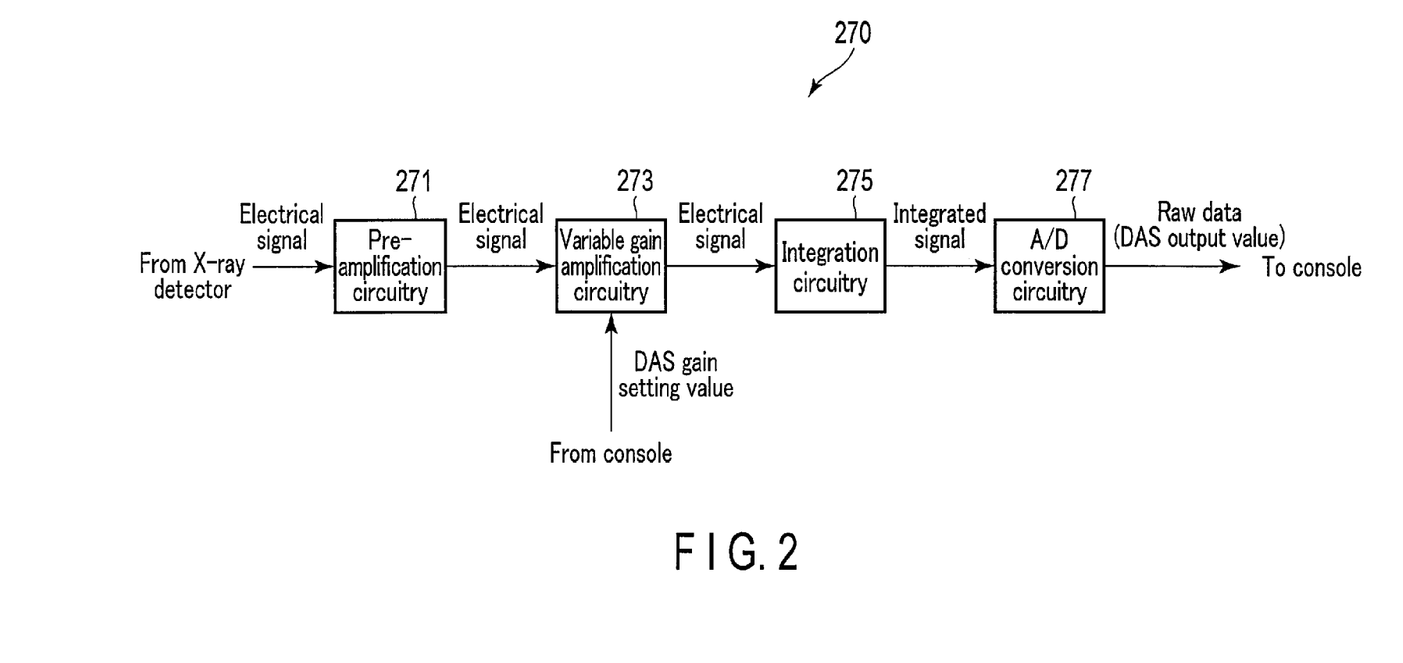
FIG. 2 is a block diagram showing the schematic arrangement of the DAS element of data acquisition circuitry in FIG. 1.

FIG. 2 is a block diagram showing the schematic arrangement of a DAS element 270 of the data acquisition circuitry 27. The DAS element 270 includes pre-amplification circuitry 271, variable gain amplification circuitry 273, integration circuitry 275, and A/D conversion circuitry 277. The pre-amplification circuitry 271 amplifies an electrical signal corresponding to the intensity of X-rays and supplied from a detector element by a predetermined gain. The variable gain amplification circuitry 273 amplifies the electrical signal from the pre-amplification circuitry 271 by a variable gain. The gain of the variable gain amplification circuitry 273 will be referred to as a DAS gain hereinafter. The DAS gain is defined by a plurality of discrete steps (levels). The variable gain amplification circuitry 273 can set the DAS gain to one of the plurality of levels. The setting value of the DAS gain is decided by processing circuitry 107 of the console 100. The setting values of the DAS gain are set to the same value throughout the detector arrays and detector channels. The integration circuitry 275 integrates the electrical signal supplied from the variable gain amplification circuitry 273 for one view period to generate an integrated signal. The integrated signal has a peak value corresponding to the dose of X-rays detected by the X-ray detector of the connection source for one view period. The A/D conversion circuitry 277 converts the integrated signal from the integration circuitry 275 from an analog signal to a digital signal (raw data). Raw data of each view is thus acquired. Raw data is a set of digital values (DAS output values) representing the dose of X-rays identified by the channel number and the column number of the detector element of the connection source and a view number representing an acquired view. The raw data is supplied to the console 100 via, for example, a noncontact data transmission unit (not shown) stored in the gantry 10. Note that another circuitry element such as an IV converter may be implemented in the data acquisition circuitry 27. The set of the pre-amplification circuitry 271, the variable gain amplification circuitry 273, the integration circuitry 275, and the A/D conversion circuitry 277 is provided for each detector element. However, at least one element of the pre-amplification circuitry 271, the variable gain amplification circuitry 273, the integration circuitry 275, and the A/D conversion circuitry 277 may be provided in correspondence with the plurality of detector elements. The data acquisition circuitry 27 includes a semiconductor integrated circuit such as an ASIC (Application Specific Integrated Circuit). The above-described circuitry elements such as the pre-amplification circuitry 271, the variable gain amplification circuitry 273, the integration circuitry 275, and the A/D conversion circuitry 277 are implemented on the semiconductor integrated circuit.

The gantry control circuitry 29 synchronously controls the high voltage generator 17, the rotation actuator 21, the bed actuator 25, and the data acquisition circuitry 27 to execute X-ray CT scan based on scan conditions from system control circuitry 115 of the console 100. In this embodiment, the gantry control circuitry 29 synchronously controls the high voltage generator 17, the rotation actuator 21, the bed actuator 25, and the data acquisition circuitry 27 to execute positioning scan and directional modulation scan. The gantry control circuitry 29 includes, as hardware resources, a processing device (processor) such as a CPU (Central Processing Unit) or an MPU (Micro Processing Unit) and storage devices (memories) such as a ROM (Read Only Memory) and a RAM (Random Access Memory). The gantry control circuitry 29 may be implemented by an ASIC (Application Specific Integrated Circuit), an FPGA (Field Programmable Logic Device), a CPLD (Complex Programmable Logic Device), or an SPLD (Simple Programmable Logic Device).

As shown in FIG. 1, the console 100 includes preprocessing circuitry 101, reconstruction circuitry 103, image processing circuitry 105, the processing circuitry 107, display circuitry 109, input circuitry 111, main storage circuitry 113, and the system control circuitry 115. Data communication between the preprocessing circuitry 101, the reconstruction circuitry 103, the image processing circuitry 105, the processing circuitry 107, the display circuitry 109, the input circuitry 111, the main storage circuitry 113, and the system control circuitry 115 is performed via a bus.

The preprocessing circuitry 101 includes, as hardware resources, a processor such as a GPU (Graphics Processing Unit) and storage devices such as a ROM and a RAM. The preprocessing circuitry 101 performs preprocessing such as logarithmic transformation for raw data transmitted from the gantry 10. The raw data after the preprocessing is also called projection data.

The reconstruction circuitry 103 includes, as hardware resources, processors such as a CPU or an MPU and a GPU and memories such as a ROM and a RAM. The reconstruction circuitry 103 generates a CT image that expresses the spatial distribution of CT values concerning the object O based on the raw data after the preprocessing. The reconstruction circuitry 103 also generates a positioning image to be used to position the object based on raw data acquired by positioning scan. As the image reconstruction algorithm, an existing image reconstruction algorithm, for example, an analytic image reconstruction method such as FBP (Filtered Back Projection) or CBP (Convolution Back Projection) or a statistical image reconstruction method such as ML-EM (Maximum Likelihood Expectation Maximization) or OS-EM (Ordered Subset Expectation Maximization) is used.

The image processing circuitry 105 performs various kinds of image processing for the CT image reconstructed by the image reconstruction circuitry 103. For example, the image processing circuitry 105 performs three-dimensional image processing such as volume rendering, surface volume rendering, image value projection processing, MPR (Multi-Planer Reconstruction) processing, and CPR (Curved MPR) processing for the CT image to generate a display image. The image processing circuitry 105 includes, as hardware resources, processors such as a CPU or an MPU and a GPU and memories such as a ROM and a RAM. The image processing circuitry 105 may be implemented by an ASIC, an FPGA, a CPLD, an SPLD, or the like.

The processing circuitry 107 includes, as hardware resources, processors such as a CPU and a GPU and memories such as a ROM and a RAM. The processing circuitry 107 executes a program (to be referred to as a scan condition decision program hereinafter) concerning decision of scan conditions for directional modulation scan. By executing the scan condition decision program, the processing circuitry 107 decides a tube current modulation condition and a DAS gain in directional modulation scan based on a positioning image concerning the object to keep the DAS gain at a value as high as possible while avoiding overflow of the data acquisition circuitry 27. More specifically, the processing circuitry 107 according to the embodiment executes the scan condition decision program, thereby implementing an AEC calculation function 121, a DAS output value calculation function 123, an overflow determination function 125, an oblateness calculation function 127, and a tube current/gain adjustment function 129.

In the AEC calculation function 121, the processing circuitry 107 performs AEC (Auto Exposure Control) calculation. More specifically, the processing circuitry 107 decides a tube current modulation condition and a DAS gain for directional modulation scan based on the body thickness information of the object. The body thickness information may be positioning image data concerning the object O or may be a body thickness measurement value. The positioning image data may be raw data (detection data) acquired by positioning scan or may be a positioning image. The processing circuitry 107 calculates the provisional value of the tube current modulation condition for directional modulation scan based on, for example, the positioning image. The modulation condition is calculated for each predetermined irradiation direction (the rotation angle about the rotation axis AR of the X-ray tube 13) for each of a plurality of slices included in the imaging range of directional modulation scan. The modulation condition may be defined by the tube current value itself or may be defined by a ratio to a reference tube current value. In this embodiment, the provisional value means a value used in adjustment before a decided value. The body thickness measurement value is defined by the body thickness value of the object O measured by a measuring instrument. The measuring instrument includes all measuring instruments capable of directly or indirectly measuring the body thickness value of the object O, such as an optical measuring instrument, an ultrasonic thickness meter, a magnetic thickness meter, a mechanical measuring instrument, and a tape measure. As such a measuring instrument, a laser projector provided in the gantry 10 may be used. The body thickness measurement value is measured from one or a plurality of angles about the long axis of the object. For example, the body thickness measurement value is measured from two angles in the AP direction and the LR direction. The tube current modulation condition and the DAS gain are decided based on the body thickness measurement values from the plurality of angles.

In the DAS output value calculation function 123, the processing circuitry 107 predicatively calculates the spatial distribution (profile) of DAS output values of the data acquisition circuitry 27 in the channel direction or column direction based on the provisional value of the modulation condition calculated by the AEC calculation function 121. The profile is calculated for each of a plurality of slices (axial sections) of the object O included in the imaging range of positioning scan or directional modulation scan.

In the overflow determination function 125, for each of the plurality of slices, the processing circuitry 107 determines, based on the spatial distribution of DAS output values calculated by the DAS output value calculation function 123, whether overflow occurs.

In the oblateness calculation function 127, the processing circuitry 107 calculates the oblateness of the object in a predetermined slice of the plurality of slices based on the positioning image. The predetermined slice is set to, for example, a slice determined to a slice where overflow occurs by the overflow determination function 125. The oblateness of the object represents the object shape in the slice as an index. The oblateness of the object is defined by object body thicknesses in the long axis direction and short axis direction, the water equivalent thickness of the object, or the ratio of the tube current value.

In the tube current/gain adjustment function 129, the processing circuitry 107 adjusts the tube current and the DAS gain. In addition, the processing circuitry 107 decides the tube current modulation condition and the DAS gain in directional modulation scan based on the object shape, more specifically, the oblateness calculated by the oblateness calculation function 127. More specifically, if a predetermined slice in which the oblateness of the object is equal to or larger than a predetermined value exists in the plurality of slices, the processing circuitry 107 decreases the provisional value of the modulation condition in the long axis direction of the object.

The display circuitry 109 displays various kinds of data such as a two-dimensional CT image and a display image. More specifically, the display circuitry 109 includes display interface circuitry and a display device. The display interface circuitry converts data representing a display target into a video signal. The video signal is supplied to the display device. The display device displays the video signal representing the display target. As the display device, for example, a CRT display, a liquid crystal display, an organic EL display, an LED display, a plasma display, or another arbitrary display known in the technical field can appropriately be used.

The input circuitry 111 inputs various kinds of instructions from the user. More specifically, the input circuitry 111 includes an input device and input interface circuitry. The input device accepts various kinds of instructions from the user. As the input device, a keyboard, a mouse, various kinds of switches, or the like can be used. The input interface circuitry supplies an output signal from the input device to the system control circuitry 115 via the bus.

The main storage circuitry 113 is a storage device configured to store various kinds of information, such as an HDD (Hard Disk Drive), an SSD (Solid State Drive), or an integrated circuit storage device. The main storage circuitry 113 may be a driving device or the like configured to read/write various kinds of information from/to a portable storage medium such as a CD-ROM drive, a DVD drive, or a flash memory. For example, the main storage circuitry 113 stores the data of a CT image and a display image. The main storage circuitry 113 also stores a control program and the like concerning directional modulation scan according to this embodiment.

The system control circuitry 115 includes, as hardware resources, a processor such as a CPU or an MPU and memories such as a ROM and a RAM. The system control circuitry 115 may be implemented by an ASIC, an FPGA, a CPLD, or an SPLD. The system control circuitry 115 functions as the core of the X-ray computed tomography apparatus according to this embodiment. More specifically, the system control circuitry 115 reads out a control program stored in the main storage circuitry 113, loads it onto the memory, and controls the units of the X-ray computed tomography apparatus in accordance with the loaded control program.

An example of the operation of the X-ray computed tomography apparatus according to this embodiment will be described next.

Figure 3:
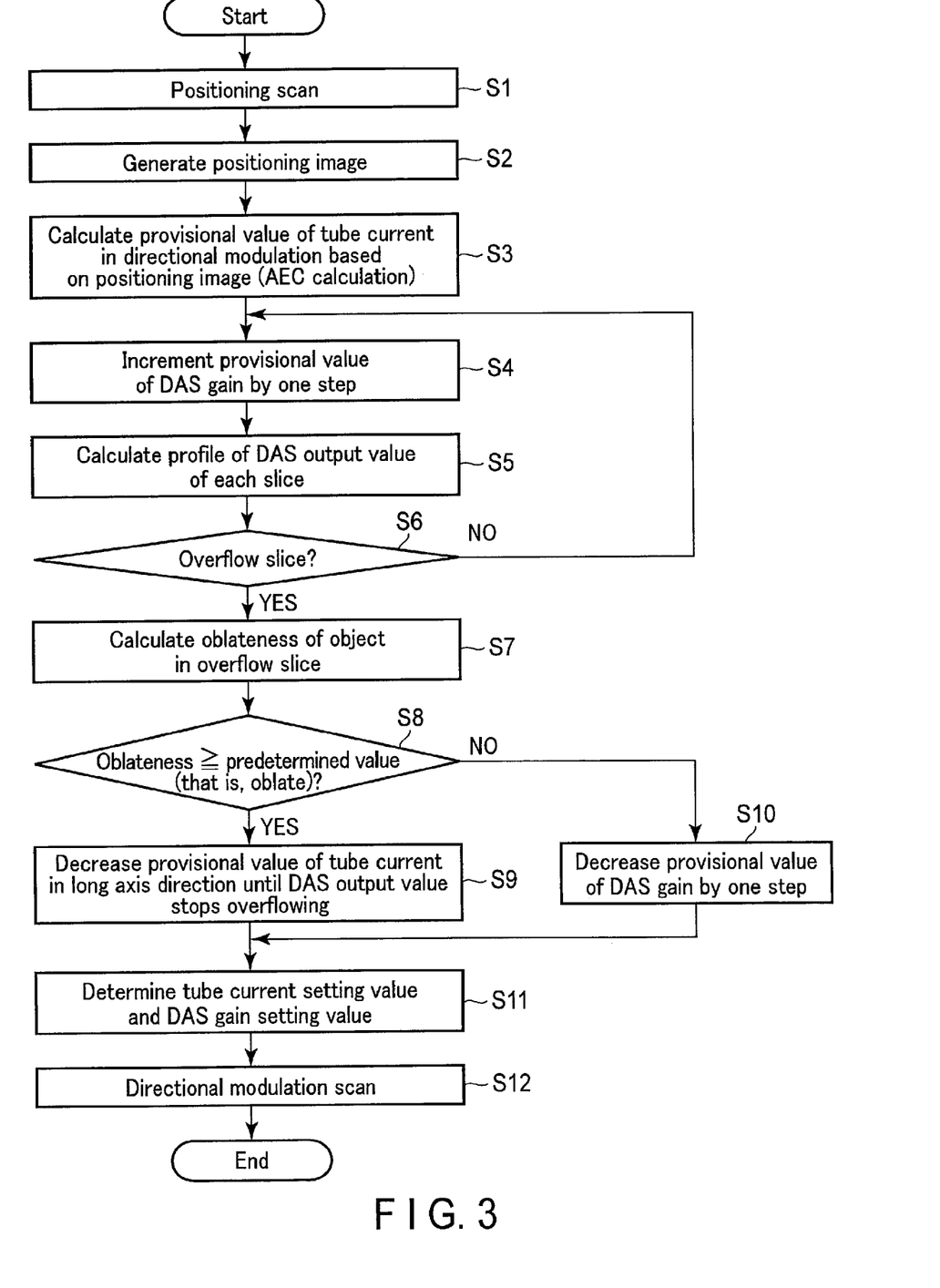
FIG. 3 is a flowchart showing the typical procedure of a series of operations of the X-ray computed tomography apparatus performed under the control of system control circuitry according to the embodiment.

FIG. 3 is a flowchart showing the typical procedure of a series of operations of the X-ray computed tomography apparatus performed under the control of the system control circuitry 115 according to the embodiment.

As shown in FIG. 3, the system control circuitry 115 causes the gantry control circuitry 29 to execute positioning scan (step S1). In step S1, the gantry control circuitry 29 synchronously controls the high voltage generator 17, the rotation actuator 21, the bed actuator 25, and the data acquisition circuitry 27 to execute positioning scan based on scan conditions concerning the positioning scan. As the positioning scan according to this embodiment, for example, scanography without rotating the rotation frame 11 is performed. In scanography, the gantry control circuitry 29 arranges the X-ray tube 13 at a predetermined rotation angle, and in a state in which the rotation frame 11 is fixed, performs X-ray radiation from the X-ray tube 13 while controlling the bed actuator 25 to move the bed top within a predetermined imaging range. The predetermined imaging range is set to a range including the scan range of directional modulation scan that is main scan. The predetermined rotation angle can be set to any angle, and is preferably set to 0° or 180° corresponding to the AP direction and 90° or 270° corresponding to the LR direction. In this case, scanography is performed twice in the AP direction and in the LR direction. In scanography in the AP direction, the data acquisition circuitry 27 acquires raw data concerning the object O via the X-ray detector 15. Similarly, in scanography in the LR direction, the data acquisition circuitry 27 acquires raw data concerning the object O via the X-ray detector 15. The acquired raw data are transmitted to the console 100.

When step S1 is performed, the system control circuitry 115 causes the reconstruction circuitry 103 to perform image generation processing (step S2). In step S2, the reconstruction circuitry 103 generates a positioning image concerning the object O based on the raw data acquired in step S1. If scanography in the AP direction is performed in step S1, the reconstruction circuitry 103 generates a scanogram image that is a projection image of the object O from the AP direction based on the raw data. Similarly, if scanography in the LR direction is performed in step S1, the reconstruction circuitry 103 reconstructs a scanogram image that is a projection image of the object O from the LR direction. The scanogram images are stored in the main storage circuitry 113.

Note that the positioning scan according to this embodiment is not limited to scanography and can be any scan as long as the shape of the object O within the predetermined imaging range can be grasped. For example, the positioning scan according to this embodiment may be helical scan that is performed while rotating the rotation frame 11. In this case, the gantry control circuitry 29 rotates the rotation frame 11 at a high speed, and in this state, performs X-ray radiation from the X-ray tube 13 while controlling the bed actuator 25 to move the bed top within a predetermined imaging range. The predetermined imaging range is set to a range including the scan range of directional modulation scan that is main scan. In helical scan, the data acquisition circuitry 27 acquires raw data concerning the object O via the X-ray detector 15. The reconstruction circuitry 103 reconstructs volume data concerning a three-dimensional CT image of the object O within the predetermined imaging range based on the acquired raw data. The reconstructed three-dimensional CT image is used as a positioning image in the following steps.

The positioning image according to this embodiment is an image generated by scan by the X-ray computed tomography apparatus. However, the positioning image is not limited to this if the shape of the object within the imaging range of directional modulation scan can be grasped. The positioning image may be an image generated by another medical modality such as a magnetic resonance imaging apparatus or a nuclear medicine diagnostic apparatus or may be an image generated by an optical camera or the like. Note that directional modulation scan is applicable to both helical scan and conventional scan performed without moving the bed top during scan.

When step S2 is performed, the system control circuitry 115 causes the processing circuitry 107 to execute the scan condition program to decide the tube current modulation condition and the DAS gain for directional modulation scan. To make a detailed description below, the tube current modulation condition is assumed to be a tube current value itself.

First, the processing circuitry 107 executes the AEC calculation function 121 (step S3). In step S3, the processing circuitry 107 calculates the provisional value of the tube current in directional modulation scan based on the positioning image generated in step S2. The provisional value calculation method will be described below in detail with reference to FIG. 4.

Figure 4:
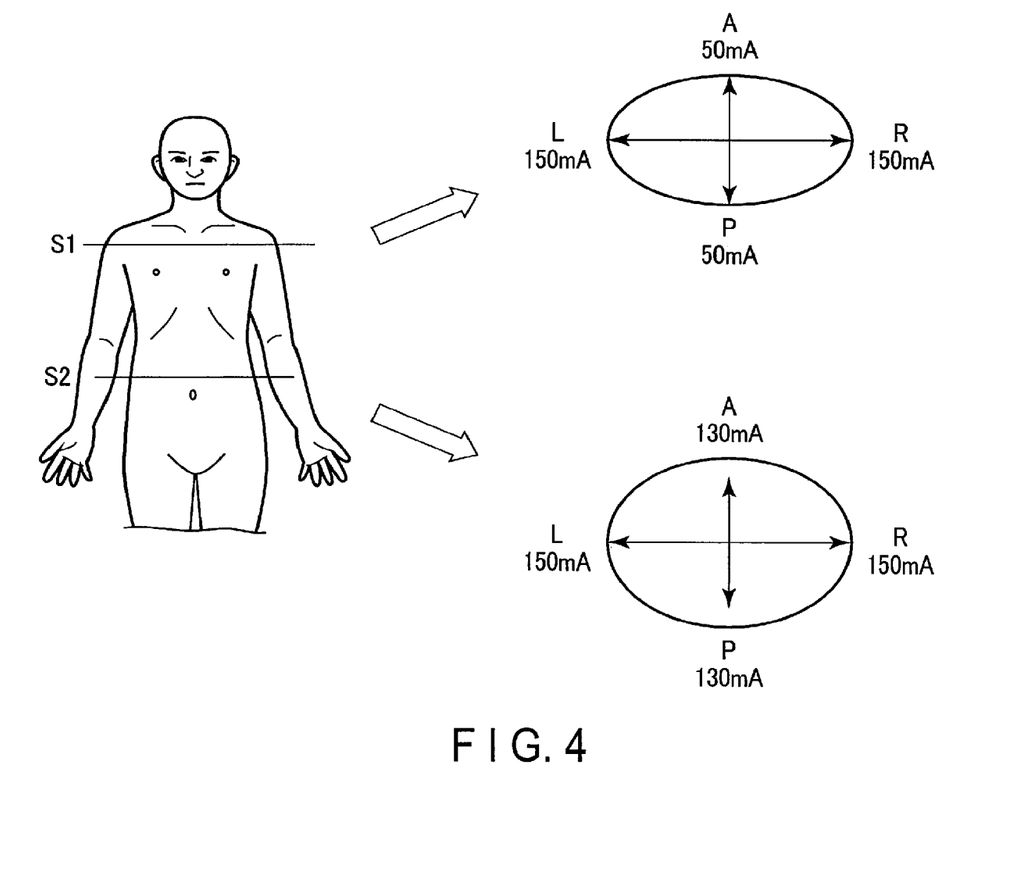
FIG. 4 is a view showing the outline of decision processing of a modulation condition for directional modulation in step S3 of FIG. 3.

FIG. 4 is a view showing the outline of decision processing of a modulation condition for directional modulation in step S3. As shown in FIG. 4, the processing circuitry 107 first calculates an object body thickness for each slice Sn (n is a slice number). Note that the slice according to this embodiment corresponds to an axial section. More specifically, the processing circuitry 107 calculates the object body thickness in each slice Sn based on the pixel value (CT value) of each pixel of the positioning image. A case in which the positioning image is a scanogram image and a case in which the positioning image is a three-dimensional image will be explained separately below.

In the case in which the positioning image is a scanogram image, for example, the processing circuitry 107 calculates the object body thickness in each pixel based on the pixel value of the pixel. The processing circuitry 107 calculates the average value of object body thicknesses in all pixels of the slice as the object body thickness in the slice. The object body thickness is the thickness in the X-ray irradiation direction when scanning the positioning image. For example, for the positioning image in the LR direction, the object body thickness in the LR direction is calculated. The object body thickness is calculated as a thickness in a case in which the whole structure of the object is assumed to be water, that is, a water equivalent thickness. The processing circuitry 107 includes an LUT (Look Up Table, which will be referred to as an AEC table) that associates a water equivalent thickness with a tube current value in advance for each of a plurality of DAS gains. The tube current value is an optimum value for the corresponding water equivalent thickness in each DAS gain. For this reason, if data acquisition is performed under the tube current value and the DAS gain, the data acquisition circuitry 27 does not cause overflow. The processing circuitry 107 decides the tube current value from the calculated water equivalent thickness using the AEC table. The decided tube current value is handled as a provisional value. In this way, the processing circuitry 107 calculates the provisional value of the tube current in the LR direction based on the positioning image in the LR direction, and calculates the provisional value of the tube current in the AP direction based on the positioning image in the AP direction. The rotation angle between the LR direction and the AP direction is decided by linear interpolation or higher-order interpolation based on the provisional value of the tube current in the LR direction and the provisional value of the tube current in the AP direction.

In the case in which the positioning image is a three-dimensional image, the processing circuitry 107 extracts an image region (to be referred to as an object region hereinafter) concerning the object included in the three-dimensional image by image processing, and detects an image region (to be referred to as a skin region hereinafter) concerning a skin in the extracted object region by image processing. The processing circuitry 107 then calculates the distance between skin regions in an arbitrary calculation target direction such as the LR direction or the AP direction, and sets the calculated distance to the object body thickness in the calculation target direction. The calculation target direction can arbitrarily be set via the input circuitry 111 or the like.

As shown in FIG. 4, in a case of a slice S1 of a shoulder portion, since the shoulder portion is flat in the slice, the object body thickness in the LR direction is large, and the object body thickness in the AP direction is small. Hence, the tube current value in the LR direction is set to be larger than the tube current value in the AP direction. For example, the tube current value in the LR direction is set to 150 mA, and the tube current value in the AP direction is set to 50 mA. In a case of a slice S2 of an abdominal portion, the abdominal portion is not flat in a slice of an object that tends to be overweight. Hence, the object body thickness in the LR direction and the object body thickness in the AP direction are almost equal. Accordingly, the tube current value in the LR direction and the tube current value in the AP direction are set to almost the same value. For example, the tube current value in the LR direction is set to 150 mA, and the tube current value in the AP direction is set to 130 mA. Note that in the slice S1 of the shoulder portion, the object body thickness in the LR direction is large, and the object body thickness in the AP direction is small. Hence, the LR direction is defined as the long axis direction, and the AP direction is defined as the short axis direction.

When step S3 is performed, the processing circuitry 107 executes the tube current/gain adjustment function 129 (step S4). In step S4, the processing circuitry 107 increments the provisional value of the DAS gain by one step from the initial value. The initial value is set to an arbitrary value other than the maximum value.

When step S4 is performed, the processing circuitry 107 executes the DAS output value calculation function 123 (step S5). In step S5, the processing circuitry 107 calculates the profile of DAS output values for each slice Sn.

Figure 5:
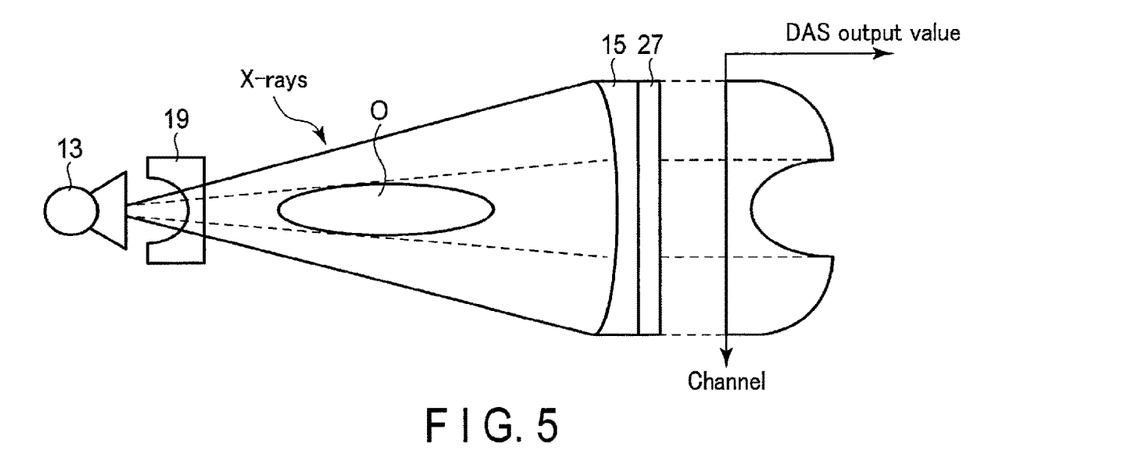
FIG. 5 is a view showing the profile of a DAS output value in the LR direction in step S5 of FIG. 3.

FIG. 5 is a view showing the profile of DAS output values in the LR direction. As shown in FIG. 5, to reduce X-rays (direct rays) that directly reach the X-ray detector 15 without passing through the object O, the bow-tie filter 19 is arranged on the X-ray emission window of the X-ray tube 13. When the bow-tie filter 19 is arranged, the dose of direct rays entering the X-ray detector 15 can be reduced. The processing circuitry 107 predictively calculates the profile of DAS output values based on a geometry model created in advance using the X-ray tube 13, the X-ray detector 15, the bow-tie filter 19, the data acquisition circuitry 27, the object O, and the like as calculation elements. In step S5, the processing circuitry 107 applies, as input conditions, the tube current value decided in step S3 and the DAS gain raised in step S4 to the geometry model, thereby calculating the profile of DAS output values. The profile of DAS output values is calculated for each slice in a predetermined irradiation direction. As for the predetermined irradiation direction, for example, the calculation may be done in the LR direction and the AP direction, or the calculation may be done in a direction other than the LR direction and the AP direction. Alternatively, the calculation may be done in one of the LR direction and the AP direction as the predetermined irradiation direction.

Assume that the object O has a flat shape in a slice, that is, the object body thickness in the LR direction is large, and the object body thickness in the AP direction is small, as in the shoulder portion, as shown in FIG. 5. In this case, even if the bow-tie filter 19 is provided, it is still feared that overflow may occur because the detection range of direct rays in the channel direction is wide. Overflow is a phenomenon in which the linearity between the dose of incident X-rays and the DAS output value is distorted because the dose of X-rays reaching a detector element per unit time is excessive.

When step S5 is performed, the processing circuitry 107 executes the overflow determination function 125 (step S6). In step S6, the processing circuitry 107 determines, based on the DAS output values calculated in step S4, whether a slice where overflow occurs exists among the plurality of slices Sn. More specifically, the processing circuitry 107 performs overflow determination for the slices Sn. Hereinafter, an overflow slice will be referred to as a slice where overflow occurs.

Figure 6:
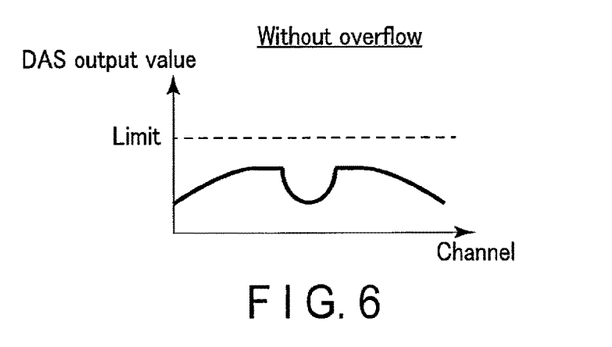
FIG. 6 is a graph for explaining overflow determination in step S6 of FIG. 3.
Figure 7:
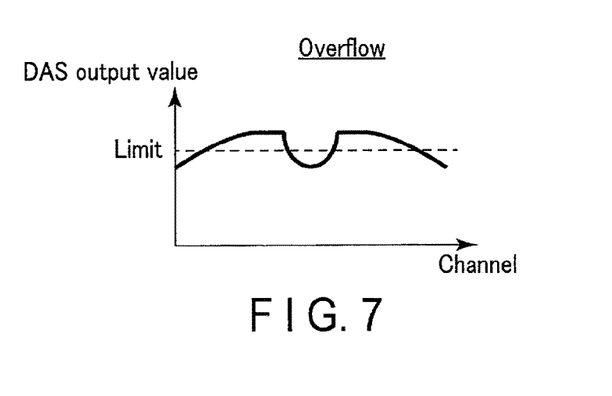
FIG. 7 is another graph for explaining overflow determination in step S6 of FIG. 3.

FIGS. 6 and 7 are graphs for explaining overflow determination in step S6. In FIGS. 6 and 7, the ordinate defines a DAS output value, and the abscissa defines a channel direction. As shown in FIGS. 6 and 7, the processing circuitry 107 compares the DAS output value of each channel with a predetermined threshold Limit. The threshold Limit is set to a DAS output value on the borderline where the data acquisition circuitry 27 causes overflow or not. The threshold Limit is experimentally determined and can be set to an arbitrary value via the input circuitry 111 or the like. As shown in FIG. 6, if a DAS output value larger than the threshold Limit does not exist in each slice, the processing circuitry 107 determines that the slice does not cause overflow. As shown in FIG. 7, if a DAS output value larger than the threshold Limit exists in each slice, the processing circuitry 107 determines that the slice causes overflow.

Upon determining in step S6 that an overflow slice does not exist (NO in step S6), the processing circuitry 107 increments the provisional value of the DAS gain by one more step (step S4). Based on the provisional value of the DAS gain incremented by one step, the processing circuitry 107 calculates the profile of DAS output values for each slice in a predetermined irradiation direction (step S5), and determines, based on the DAS output values, whether an overflow slice exists (step S6).

Upon determining in step S6 that an overflow slice exists (YES in step S6), the processing circuitry 107 executes the oblateness calculation function 127 (step S7). In step S7, the processing circuitry 107 calculates the oblateness of the object in the overflow slice. More specifically, the processing circuitry 107 calculates the ratio of object body thicknesses in two directions that are almost orthogonal in the overflow slice. If the positioning image is a scanogram image, the processing circuitry 107 typically calculates the oblateness in accordance with the following procedure. First, the processing circuitry 107 calculates a water equivalent thickness based on the CT value of each pixel of the scanogram image in the LR direction, calculates the average value of the water equivalent thicknesses in all pixels, and sets the calculated average value to the object body thickness in the LR direction. Similarly, the processing circuitry 107 calculates a water equivalent thickness based on the CT value of each pixel of the scanogram image in the AP direction, calculates the average value of the water equivalent thicknesses in all pixels, and sets the calculated average value to the object body thickness in the AP direction. Next, the processing circuitry 107 calculates the ratio of the object body thickness in the LR direction to the object body thickness in the AP direction as the oblateness.

Note that the oblateness calculation method is not limited to the above-described method. For example, since the tube current value and the object body thickness decided by the AEC calculation have a correlation, the processing circuitry 107 may calculate the ratio of the provisional value of the tube current in the LR direction to the provisional value of the tube current in the AP direction as the oblateness of the object.

When step S7 is performed, the processing circuitry 107 determines whether the oblateness calculated in step S7 is equal to or larger than a predetermined value (step S8). The predetermined value is the value of the oblateness on the borderline where the object is flat or not and can arbitrarily be set via the input circuitry 111. That is, if the oblateness is equal to or larger than the predetermined value, the object is determined to be flat. If the oblateness is less than the predetermined value, the object is determined to not be flat.

Upon determining in step S8 that the oblateness is equal to or larger than the predetermined value, that is, the object is flat (YES in step S8), the processing circuitry 107 executes the tube current/gain adjustment function 129 (step S9). In step S9, the processing circuitry 107 lowers the provisional value of the tube current in the long axis direction until the DAS output value stops overflowing.

Upon determining in step S8 that the oblateness is less than the predetermined value, that is, the object is not flat (NO in step S8), the processing circuitry 107 executes the tube current/gain adjustment function 129 (step S10). In step S10, the processing circuitry 107 decreases the provisional value of the DAS gain by one step.

When step S9 or S10 is performed, the processing circuitry 107 decides the currently set provisional value of the tube current to a tube current setting value, and decides the provisional value of the DAS gain to a DAS gain setting value. The tube current setting value and the DAS gain setting value are stored in the main storage circuitry 113 as scan conditions for directional modulation scan.

Figure 8:
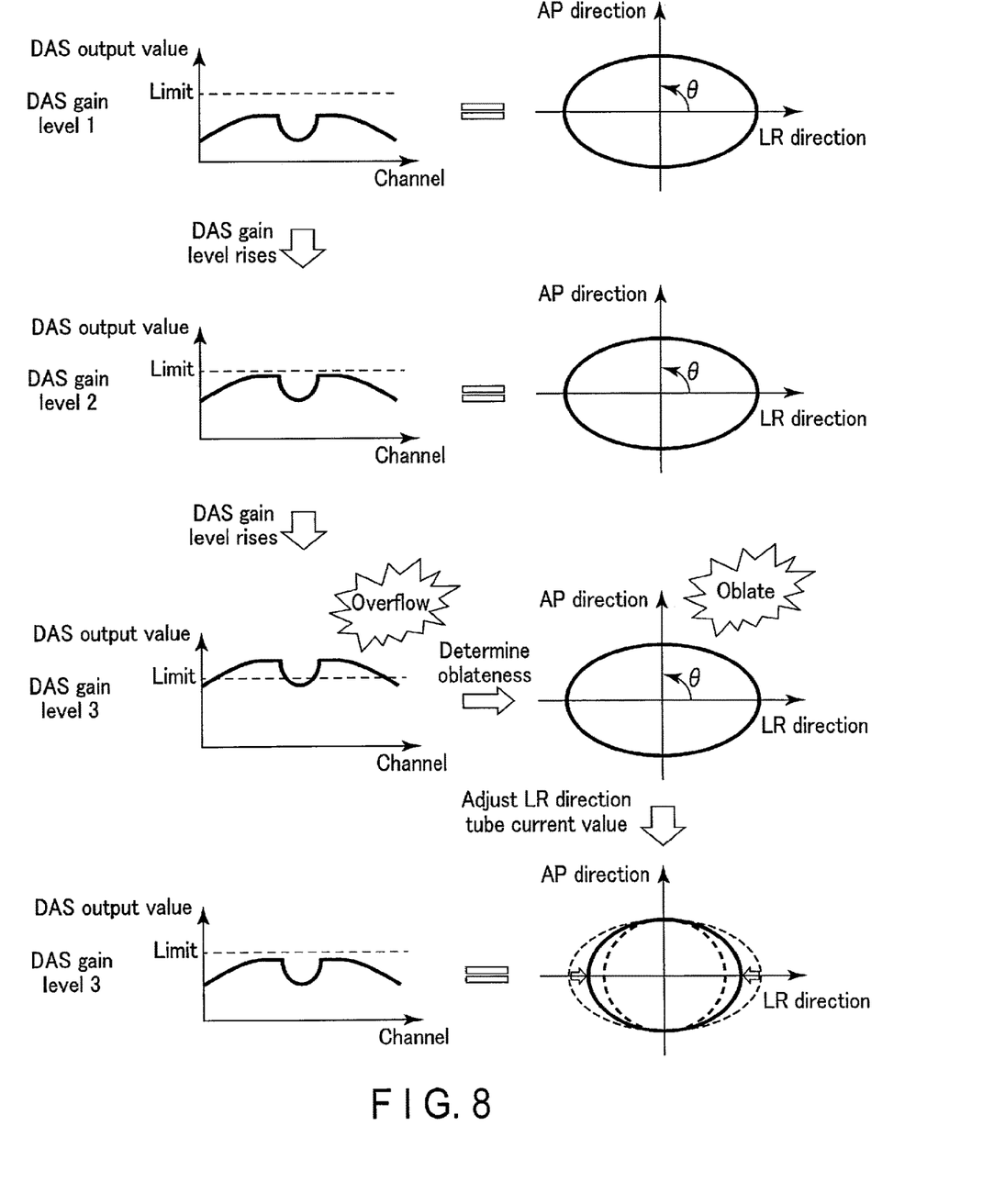
FIG. 8 is a view schematically showing the process in steps S3 to S11 of FIG. 3.

The process in steps S3 to S11 will be described here with reference to FIG. 8. FIG. 8 is a view schematically showing the process in steps S3 to S11. FIG. 8 shows the course of the process for a single slice. However, the process shown in FIG. 8 is performed for all slices in a similar manner. This will be described below in detail.

As shown on the right side of the uppermost stage of FIG. 8, under a DAS gain of level 1, AEC calculation is executed in step S3 to provisionally calculate the tube current value in directional modulation for each irradiation direction θ. The irradiation direction θ may be calculated continuously in 360°, as shown in FIG. 8, or may be calculated discretely at 0°, 90°, 180°, and 270°. Initially, as shown on the left side of the uppermost stage of FIG. 8, the tube current value is set to a value that prevents the DAS output value from causing overflow. After step S3, the DAS gain is raised to level 2 in step S4, as shown on the right side of the second stage of FIG. 8. Along with the raise of the DAS gain, the DAS output values equally increase in all channels. In step S6, overflow determination is performed under the DAS gain of level 2. In a case shown in the second stage of FIG. 8, since the DAS output values are less than the threshold Limit in all channels, the process returns to step S4. The DAS gain is raised to level 3 in step S4, as shown on the left side of the third stage of FIG. 8. Along with the raise of the DAS gain, the DAS output values equally increase in all channels. In step S6, overflow determination is performed under the DAS gain of level 3. In a case shown in the third stage of FIG. 8, since a channel where the DAS output value is larger than the threshold limit exists, it is determined in step S6 that overflow occurs. Since it is determined that overflow occurs, the oblateness of the object is calculated in step S7. In step S8, it is determined whether the object is flat. In a case shown in on the right side of the third stage of FIG. 8, since the object body thickness (tube current value) in the long axis direction (LR direction) is relatively larger than the object body thickness (tube current value) in the short axis direction (AP direction), it is determined that the object is flat.

In this case, the processing circuitry 107 decreases the tube current value in the long axis direction (LR direction) in step S9 until overflow is eliminated, as shown on the right side of the lowermost stage of FIG. 8. A dot line on the right side of the lowermost stage of FIG. 8 indicates the tube current value before the decrease, a long broken line indicates a tube current value having the same value as the tube current value in the AP direction, and a solid line indicates the tube current value after the decrease. In FIG. 8, the processing circuitry 107, for example, decreases the tube current value in the LR direction toward the tube current value in the AP direction. The processing circuitry 107 may decrease the tube current value in the LR direction up to the tube current value in the AP direction by one time of decrease, or may decrease the tube current value in the LR direction up to the tube current value in the AP direction divisionally by multiple times of decrease. In the latter case, the processing circuitry 107 first decreases the tube current value in the LR direction only by a predetermined value. The predetermined value is set to a value smaller than the difference value between the tube current value in the AP direction and the tube current value in the LR direction. The processing circuitry 107 calculates the DAS output value for the tube current value after the decrease and performs overflow determination. Upon determining that overflow occurs, the processing circuitry 107 further decreases the tube current value in the LR direction toward the tube current value in the AP direction, calculates the DAS output value for the tube current value after the decrease, and performs overflow determination again. In this way, the processing circuitry 107 repetitively decreases the tube current value in the LR direction until it determines that an overflow does not occur. Upon determining that overflow does not occur, the processing circuitry 107 sets the tube current value when determining that overflow does not occur to the tube current setting value, and sets the provisional value of the DAS gain to the DAS gain setting value.

Note that upon determining in step S8 that the oblateness is not equal to or larger than the predetermined value, the processing circuitry 107 lowers the DAS gain from level 3 to level 2, although not illustrated in FIG. 8. If the tube current value is decreased in all directions, the dose is short in all directions. For this reason, a low count artifact conspicuously occurs in the reconstructed image. In this embodiment, the processing circuitry 107 lowers the DAS gain to maintain the dose and reduce the artifact. As described above, the DAS gain is set to a single level for all slices, all channels, and all columns. Hence, to suppress overflow in all slices, the level of the DAS gain concerning all slices is lowered in step S10.

In step S9, the processing circuitry 107 decreases only the tube current value in the long axis direction. However, the embodiment is not limited to this. The processing circuitry 107 may optimize the tube current values including not only the tube current value in the long axis direction but also tube current values in other irradiation directions. For example, the processing circuitry 107 may decrease not only the tube current value in the LR direction but also the tube current value in the AP direction so as to level out the DAS output values in all irradiation directions.

When step S11 is performed, the system control circuitry 115 waits for a directional modulation scan start instruction. When a health care worker presses a scan start button or the like via the input circuitry 111 or the like, the system control circuitry 115 causes the gantry control circuitry 29 to execute directional modulation scan (step S12). In step S12, the gantry control circuitry 29 synchronously controls the high voltage generator 17, the rotation actuator 21, the bed actuator 25, and the data acquisition circuitry 27 to execute directional modulation scan in accordance with the scan conditions such as the tube current setting value and the DAS gain setting value decided in step S11. In the directional modulation scan, the gantry control circuitry 29 first sets the DAS gain of the variable gain amplification circuitry of the data acquisition circuitry 27 to the DAS gain setting value. Then, the gantry control circuitry 29 rotates the rotation frame 11 at a high speed, controls, in this state, the high voltage generator 17 to perform X-ray radiation from the X-ray tube 13 while controlling the bed actuator 25 to move the bed top within a predetermined imaging range, and causes the data acquisition circuitry 27 to acquire raw data. At this time, the high voltage generator 17 modulates the tube current in accordance with the tube current setting value for each irradiation direction. The directional modulation scan is thus implemented. In the directional modulation scan, the data acquisition circuitry 27 acquires raw data concerning the object O via the X-ray detector 15. The reconstruction circuitry 103 reconstructs volume data concerning a three-dimensional CT image of the object O within the predetermined imaging range based on the acquired raw data. The reconstructed three-dimensional CT image is processed by the image processing circuitry 105 and displayed on the display circuitry 109.

A series of operations of the X-ray computed tomography apparatus performed under the control of the system control circuitry 115 according to the embodiment has been described above.

As shown in the operation example of FIG. 3, if an overflow slice exists, the processing circuitry 107 according to this embodiment determines whether the object shape is flat, instead of unconditionally lowering the DAS gain. Upon determining that the object shape is flat, the processing circuitry 107 decreases the modulation condition value in the long axis direction of the object, thereby avoiding overflow without lowering the DAS gain. On the other hand, upon determining that the object shape is not flat, the processing circuitry 107 determines that there is no room for decreasing the modulation condition value and lowers the DAS gain. As described above, to maintain the DAS gain at a level as high as possible while avoiding overflow of the data acquisition circuitry 27, the processing circuitry 107 according to this embodiment adjusts the tube current setting value and the DAS gain for directional modulation scan of the tube current value in consideration of the object shape in a slice, in other words, the object body thickness for each irradiation direction. The optimum tube current setting value and the DAS gain setting value can thus be set in accordance with the object shape.

Note that the procedure of the operation shown in FIG. 3 is merely an example, and the processing steps of the X-ray computed tomography apparatus according to this embodiment are not limited to these. For example, the positioning scan step of step S1 and the positioning image generation step of step S2 can be omitted if a positioning image already exists.

In the procedure of the operation shown in FIG. 3, if an overflow slice does not exist, the DAS gain is raised stepwise from a low level to a high level. However, the embodiment is not limited to this. That is, the processing circuitry 107 may set the initial value of the DAS gain to the maximum level, and every time it is determined that an overflow slice exists, lower the DAS gain stepwise from a high level to a low level.

As described above, the X-ray computed tomography apparatus according to this embodiment includes the X-ray detector 15, the data acquisition circuitry 27, and the processing circuitry 107. The X-ray detector 15 detects X-rays emitted by the X-ray tube 13 and transmitted through the object O. The data acquisition circuitry 27 amplifies an electrical signal corresponding to the detected X-rays by a variable gain. The processing circuitry 107 decides the modulation condition of the tube current in directional modulation scan and the DAS gain of the data acquisition circuitry 27 based on body thickness information concerning the object O so as to avoid overflow of the data acquisition circuitry 27 while maintaining the DAS gain at a level as high as possible.

With the above-described arrangement, the processing circuitry 107 can decide the optimum tube current modulation condition and the DAS gain according to the shape of the object. It is therefore possible to optimize the image quality and reduce exposure of the object O by extension.

Hence, according to this embodiment, it is possible to optimally adjust the image quality and dose in directional modulation scan.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
an X-ray detector that detects X-rays emitted by an X-ray tube and transmitted through an object and outputs an electrical signal concerning the detected X-rays;
data acquisition circuitry that amplifies the electrical signal by a variable gain and acquires detection data based on the amplified electrical signal; and
processing circuitry that decides the gain and a modulation condition of a tube current in a directional modulation scan based on body thickness information of the object,
wherein the processing circuitry:
calculates an oblateness value of the object in a predetermined slice by specifying a ratio of body thicknesses in a long axis direction and a short axis direction based on a scanogram image,
if the oblateness value is not less than a first predetermined value, decreases a provisional value of the modulation condition in the long axis direction of the object in the predetermined slice, and
if the oblateness value is less than the first predetermined value, decreases a provisional value of the gain,
wherein the provisional values are values used in adjustment before decided values.

2. The apparatus of claim 1, wherein the processing circuitry decides the provisional value of the modulation condition of the directional modulation scan based on the body thickness information, and decides a setting value of the modulation condition and a setting value of the gain based on the provisional value.

3. The apparatus of claim 1, wherein the modulation condition is a ratio of a tube current value in an AP direction to a tube current value in an LR direction.

4. The apparatus of claim 1, wherein the processing circuitry calculates the provisional value of the modulation condition for each of a plurality of slices based on the scanogram image, calculates an output value distribution of the data acquisition circuitry according to the provisional value of the modulation condition for each of the plurality of slices, specifies a slice having an output value not less than a second predetermined value from the plurality of slices, and sets the specified slice to the predetermined slice.

5. The apparatus of claim 4, wherein if the slice having the output value not less than the second predetermined value does not exist among the plurality of slices, the processing circuitry raises the provisional value of the gain.

6. The apparatus of claim 1, wherein if the oblateness value is not less than the first predetermined value, the processing circuitry decreases the provisional value of the modulation condition in the long axis direction in the predetermined slice until an output value of the data acquisition circuitry becomes not more than a second predetermined value.

7. The apparatus of claim 1, wherein if the oblateness value is not less than the first predetermined value, the processing circuitry decreases the provisional value of the modulation condition in the long axis direction of the object in the predetermined slice up to the provisional value of the modulation condition in the short axis direction of the object.

8. The apparatus of claim 1, wherein the processing circuitry calculates the oblateness value further based on a water equivalent thickness.

9. The apparatus of claim 1, further comprising:
a high voltage generator that adjusts a tube voltage and the tube current to the X-ray tube; and
gantry control circuitry that controls the high voltage generator to execute a positioning scan to position the object,
wherein the processing circuitry reconstructs the scanogram image based on the detection data acquired by the data acquisition circuitry in the positioning scan.

10. The apparatus of claim 1, wherein the processing circuitry calculates the provisional value of the modulation condition for each of a plurality of slices based on the body thickness information,
and if a slice where the data acquisition circuitry overflows exists among the plurality of slices under the provisional value of the modulation condition, sets the slice to the predetermined slice.

* * * * *